United States Patent [19]

Jakupovic et al.

[11] Patent Number: 4,925,933
[45] Date of Patent: May 15, 1990

[54] METHOD OF CONTROLLING THE EPIMERIC DISTRIBUTION IN THE PREPARATION OF 16,17-ACETALS OF PREGNANE DERIVATIVES

[75] Inventors: Edib Jakupovic, Nykvarn; Roy T. Sourander; Jan U. Stenhede, both of Södertälje; Rolf P. Svensson, Rönninge, all of Sweden

[73] Assignee: Astra Pharmaceutical Production Aktiebolag, Sodertalje, Sweden

[21] Appl. No.: 96,598

[22] Filed: Sep. 11, 1987

[30] Foreign Application Priority Data

Sep. 25, 1986 [SE] Sweden .............................. 8604059-9

[51] Int. Cl.$^5$ ............................................ C07J 17/00
[52] U.S. Cl. ...................................................... 540/63
[58] Field of Search ...................... 260/397.45, 397.1; 540/61, 63

[56] References Cited

U.S. PATENT DOCUMENTS 3,928,326 12/1975 Brattsand et al. .
3,929,768 12/1975 Brattsand et al. .

FOREIGN PATENT DOCUMENTS 0054010  6/1982 European Pat. Off. .
0164636 12/1986 European Pat. Off. .
527509  11/1983 Spain .

OTHER PUBLICATIONS

CA, vol. 100, 1984, 36922z, "Deasphalting of Hydrocarbon Oil with Solvent".

Primary Examiner—Brian E. Hearn
Assistant Examiner—Andrew Griffis
Attorney, Agent, or Firm—White & Case

[57] ABSTRACT

A method of controlling the epimeric distribution in the preparation of 16,17-acetals of pregnane derivatives characterized in reaction of a corresponding 16,17-acetonide with an aldehyde or ketone in (a) hydrocarbon solvent wherein the solubility of the pregnane derivative is less than 1 mg/l or in a halogenated hydrocarbon solvent together with a hydrohalogen acid or an organic sulphonic acid as catalyst and in the presence of small grains of an insert material in the reaction medium or (b) a halogenated hydrocarbon solvent together with a hydrohalogen acid an organic sulphonic acid as catalyst and in the presence of an epimeric distribution modifier.

7 Claims, No Drawings

METHOD OF CONTROLLING THE EPIMERIC DISTRIBUTION IN THE PREPARATION OF 16,17-ACETALS OF PREGNANE DERIVATIVES

FIELD OF THE INVENTION

The present invention concerns a process for the preparation of 16,17-acetals of pregnane derivatives through transacetalisation of the corresponding 16,17-acetonides, or by reaction of the 16,17-diol.

PRIOR ART

When aldehydes or non-symmetrical ketones are used in the transacetalisation reaction, the acetals are formed as couples of epimers, which can be separated by column chromatography as described in U.S. Pat. No. 3,928,326 and 4,404,200.

The known methods for the preparation of pregnene or pregnadiene 16,17-acetals, which are based upon the transacetalisation of 16,17-acetonides with an aldehyde in solutions or suspensions of hydrofluoric acid at low temperatures (EP 164 636), are difficult to apply industrially.

A method described in ES 8506753 for the preparation of budesonide, [(22RS)-16α,17α-butylidenedioxy-pregna-1,4-diene-11β,21-diol-3,20-dione] based upon transacetalisation of a 16α,17α-acetonide with n-butyraldehyde in an aprotic solvent and in the presence of a catalyst, such as perchloric acid, results in an undefined distribution of the 22R- and 22S-epimers.

DISCLOSURE OF THE INVENTION

The present invention refers to a method of controlling the epimeric distribution in the preparation of 16,17-acetals of pregnane derivatives having the formula I

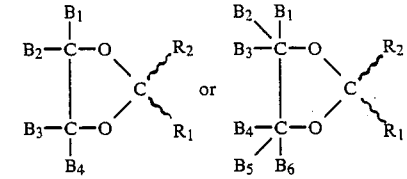 (I)

wherein the 1,2-position is saturated or unsaturated;
$R_1$ represents a $C_1-C_{12}$ straight chain or branched alkyl group;
$R_2$ is different from $R_1$ and may be hydrogen, methyl or ethyl;
$R_3$ may be hydrogen or

$-CR$ wherein R represents a $C_1-C_{12}$ straight chain or branched alkyl group;
$R_4$ may be hydrogen, fluorine or chlorine;
$R_5$ may be hydrogen, methyl, fluorine or chlorine.
$R_1$ represents particularly a n-propyl group.
$R_2$ represents particularly a hydrogen atom.

One embodiment of the invention is represented by the direction of the process in such manner that predominantly the 22R-epimer of the compound of the formula I is obtained (Embodiment A).

Another embodiment of the invention is represented by the direction of the process in such a manner that the 22R and 22S epimers are obtained in about equal proportions (Embodiment B).

The compounds of formula I are prepared by a transacetalisation process wherein a compound of the formula

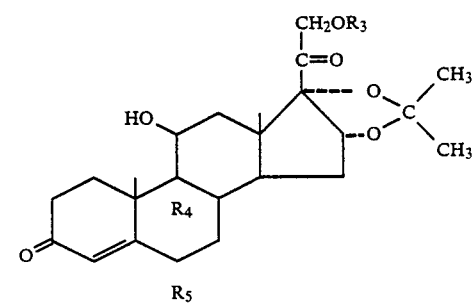

or

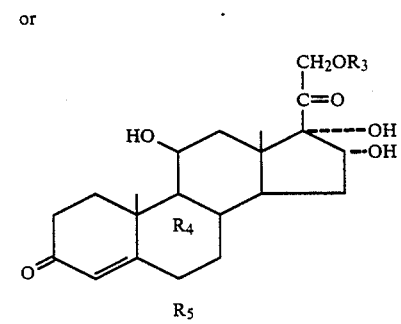

is reacted with an aldehyde or a ketone having the formula $R_1COR_2$ or its acetals

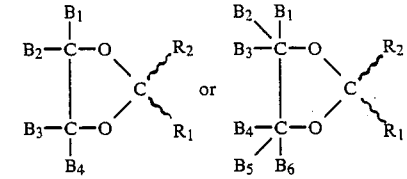

in which formulas $R_1$, $R_2$, $R_3$, $R_4$ and $R_5$ are as defined above, and $B_1$ to $B_6$ are the same or different and each representing hydrogen or alkyl group with straight or branched hydrocarbon chains having 1–10 carbon atoms, selected among methyl, ethyl, propyl, iso-propyl, butyl, iso-butyl, tert-butyl, pentyl, hexyl, heptyl, octyl, nonyl or decyl, e.g. acetals between n-butanal or n-pentanal and ethylene glycol, propylene glycol, 1,2-butanediol, 1,2-pentanediol, 2,2,4-trimethyl-1,2-pentanediol, 2,3-hexanediol, 1,2-octanediol, methanol, ethanol, propanol, iso-propanol, butanol, iso-butanol, tert-butanol, pentanol, hexanol, heptanol, di-ethylisopropyl-carbinol and 2,2,5,5-tetramethylhexanol-3.

In embodiment A wherein predominantly the 22R epimer is obtained the particular characteristics of the process are (a) the reaction is performed in a reaction medium which is a hydrocarbon wherein the solubility of the pregnane derivative (the 16,17-acetonide or the 16,17-diol) is less than 1 mg/l, or in a halogenated hydrocarbon (b) the presence of a catalyst which is a hydrohalogen acid or an organic sulphonic acid such as p-toluene sulphonic acid and (c) the presence of small grains of an inert material, such as glass, ceramic, sifted silicone dioxide (sand) or inert metal particles, such as granulated stainless steel or tantalum in the reaction medium (when the reaction is performed in a hydrocarbon solvent).

In embodiment A the most active epimer, the 22R-epimer is so exclusively obtained that it can be sufficiently purified to be used as a pharmaceutical substance by recrystallization instead of by the more expensive chromatographic procedure described in U.S. Pat. No. 3,928,326 and 4,404,200.

At the reaction procedure in hydrocarbons the steroid-catalyst complex will form a big sticky lump which makes stirring and effective reaction impossible.

The process according to the present invention allows to overcome this by the use of small grains of an inert material and effective stirring to prevent the formation of a big lump and instead divide the steroid-catalyst complex into a thin layer around the grains. Thereby, the reactive surface will be much larger and the reaction with the carbonyl compound proceeds very rapidly.

According to embodiment A, the 16,17-acetonides or 16,17-diols are reacted with aldehydes or ketones or an acetal hereof, respectively, in molar ratios ranging from 1:1 to 1.5, preferably from 1:1 to 1:2 in a hydrocarbon (preferably isooctane) in concentrations ranging from 1:5 to 1:50, preferably from 1:20 to 1:30 or in a halogenated hydrocarbon (preferably methylene chloride) in concentrations ranging from 1:50 to 1:500, preferably 1:250 at temperatures ranging from $+0°$ to $+40°$ C., preferably at $+30°$ C. The reaction is performed with a hydrohalogen acid or an organic sulphonic acid such as p-toluene sulphonic acid, preferably perchloric acid, as catalyst. The amount of catalyst will in molar ratios range from 1:1 to 1:15, preferably 1:4.

The product is isolated by aqueous $K_2CO_3$ and $CH_2Cl_2$. The $CH_2Cl$ phase is dried with $Na_2SO_4$ and concentrated in vacuum $+40°$ C.

In a preferred way to perform embodiment A of the process of the invention the most active epimer, the 22R-epimer, of 6-, 9-, or 6,9-fluorinated and non-fluorinated (22RS)-16α,17α-butylidenedioxy-11β,21-dihydroxypregna-1,4-diene-3,20-diones, is synthesized without chromatographic separation of the epimers.

The inert grain material used in the process, preferably silicone dioxide ($SiO_2$), should consist of free-flowing small particles. The particles size is ranging from 0.1–1.0 mm, preferably 0.1–0.3 mm. The amount used in the reaction will range from 1:5 to 1:50, preferably 1:20.

With hydrohalogen acid in this text is to be understood hydrofluoric, hydrochloric, hydrobromic and hydroiodic acid and the corresponding oxohalogen acids, such as perchloric acid.

In a general outline of the embodiment A the invention is carried out as follows:

Acetonide (or diol), grain material, aldehyde (or ketone) or its acetal and solvent are mixed. The catalyst is then quickly added with vigorous stirring to permit formation of small particles, facilitating the reaction.

While the reaction mixture is stirred the epimeric distribution is followed on HPLC. When desired 22R/22S epimeric distribution is obtained the reaction mixture is cooled and $K_2CO_3$ is added. Filtering yields the product attached to the grain material. After stirring the methylene chloride and filtering, a product consisting predominantly of the 22R-epimer of the compound of the formula I is obtained by evaporation of the solvent.

When an uneven epimeric distribution is desired this will be in the range 100–90/0–10 in favour of the 22R epimer.

In embodiment B, wherein the 22R/22epimeric distribution can be varied within the range 40:60–60:40, the particular characteristics of the process are (a) the reaction is performed in a halogenated hydrocarbon, such as methylene chloride or chloroform, (b) the reaction is performed with the aid of an epimeric distribution modifier, such as a chemical substance which could be dimethylsulfoxide or N,N-dimethylformamide or a particular temperature chosen in the range $-50°$ C.–$+50°$ C.

(c) the presence of an amount of a catalyst which is a hydrohalogen acid (preferably perchloric acid) or an organic sulphonic acid such as p-toluenesulphonic acid.

In embodiment B the reaction condition (a)–(c) induce accelerated reaction rate, high yield and an slightly uneven epimer distribution.

With reaction temperature within the prescribed range or addition of various amounts of dimethylsulfoxide or N,N-dimethylformamide from the beginning of the reaction or after the acetalization reaction is completed, makes possible the direction of the 22R/22S epimer distribution in the range 40:60–60:40, preferably 50:50.

In a preferred way to perform the embodiment B of the process of the invention budesonide is prepared with an epimeric distribution of about 50:50.

According to embodiment B, the 16,17-acetonides or 16,17-diols are reacted with aldehydes or ketones or an acetal thereof, respectively, in molar ratios ranging from 1:1 to 1:5, preferably from 1:1 to 1:2 in a halogenated hydrocarbon solvent (preferably methylene chloride or chloroform) in concentrations ranging from 1:2 to 1:100, preferably from 1:3 to 1:10 at temperatures ranging from $-50°$ to $+50°$ C., preferably at $+0°$ C. The reaction is performed with a hydrohalogen acid, preferably perchloric acid, or an organic sulphonic acid such as, p-toluenesulphonic acid as catalyst. The amount of catalyst in molar ratios will range from 1:1 to 1:15, preferably 1:4.

The product is isolated by aqueous $K_2CO_3$ and $CH_2Cl_2$. The $CH_2Cl_2$ phase is dried with $Na_2SO_4$ and concentrated in vacuum $+40°$ C.

In a general outline the embodiment B of the invention is carried out as follows:

Acetonide (or diol), aldehyde (or ketone) or its acetal and solvent are mixed. The catalyst is then added with vigorous stirring. The reaction mixture is stirred in low temperature ($-50°$ C.–$+50°$ C.) or with the addition of DMSO or DMF, from the beginning of the reaction or after the end point of the reaction is established on HPLC. When desired epimeric distribution is obtained (followed in HPLC) the reaction mixture is cooled and $K_2CO_3$ is added whereby the compound of the formula I with desired epimeric distribution is obtained.

In embodiment A as well as B a preferred mode is the use of 16,17-acetonides as starting materials. These compounds are stable, and easily available and can be easily purified. The acetonides are often used for the purification of diols, and can therefore be considered to be precursors of the 16,17-diols, earlier used for the preparation of non-symmetrical 16,17-acetals. Accordingly, the 16,17-acetonides have a lower production cost than the corresponding 16,17-diols.

BEST MODE OF CARRING OUT THE INVENTION

The invention will be illustrated by means of the following working example without being limited thereto.

EXAMPLE 1 (EMBODIMENT A)

Fluocinolone acetonide (40 g), 12 ml of butanal, 800 g of fine sand ($SiO_2$) and 1000 ml of heptane are mixed at room temperature.

30 ml of 70% $HClO_4$ is rapidly added under vigorous stirring. The reaction mixture is stirred at room temperature for another 5 hours and the reaction is followed in HPLC. The epimeric distribution will eventually stop at 22R/22S=97/3. The reaction mixture is cooled and 10% aqueous $K_2CO_3$ is added. The temperature is not allowed to raise above 25° C. The reaction mixture is filtered and the solid residue is washed with 500 ml of heptane and 1000 ml of $H_2O$ and stirred with methylene chloride to remove the product, which still was attached to the sand particles, and filtered.

The methylene chloride phase is washed with 200 ml of 10% aqueous $K_2CO_3$ and $2 \times 250$ ml of water, dried with $Na_2SO_4$ and concentrated in vacuum at 40° C., yielding 42 g of (22R)-16α,17α-butylidenedioxy-6α,9α-difluoro-11,21-dihydroxypregna-1,4-diene-3,20-dione mixed with 3% of the 22S-epimer. Recrystallisation from methanol-water lowered the content of 22S-epimer to 1%. Molecular weight (MS-CI): 466, M.p. 169°–72° C. $[\alpha]_D^{25} = +94.5°$ (c=0.170; $CH_2Cl_2$). $^1$H-NMR ($CDCl_3$): 0.91 (18-$CH_3$), 4.59 (22-H), 4.93 (16-H).

EXAMPLE 2 (EMBODIMENT A)

Fluocinolone acetonide (40 g), 12 ml of butanal, 800 g of fine sand ($SiO_2$) and 1000 ml of isooctane are mixed at room temperature.

30 ml of 70% $HClO_4$ is rapidly added under vigorous stirring. The reaction mixture is stirred at room temperature for another 5 hours and the reaction is followed on HPLC. The epimeric distribution will eventually stop at 22R/22S=98/2. The reaction mixture is cooled and 10% aqueous $K_2CO_3$ is added. The temperature is not allowed to raise above 25° C. The reaction mixture is filtered and the solid residue is washed with 500 ml of isooctane and 1000 ml of $H_2O$ and stirred with methylene chloride to remove the product, which still was attached to the sand particles, and filtered.

The methylene chloride phase is washed with 200 ml of 10% aqueous $K_2CO_3$ and $2 \times 250$ ml of water, dried with $Na_2SO_4$ and concentrated in vacuum at 40° C., yielding 42 g of (22R)-16α,17α-butylidenedioxy-6α,9α-difluoro-11,21-dihydroxypregna-1,4-diene-3,20-dione mixed with 2% of the 22S-epimer. Recrystallisation from methanol-water lowered the content of 22S-epimer to 1%. Molecular weight (MS-CI): 466. M.p. 169°–72° C.$[\alpha]_D^{25} = +94.5°$ (c=0.170; $CH_2Cl_2$). $^1$H-NMR ($CDCl_3$): 0.91 (18-$CH_3$), 4.59 (22-H), 4.93 (16-H).

EXAMPLE 3 (EMBODIMENT A)

Fluocinolone (10 g), 3 ml of butanol, 200 g of fine sand ($SiO_2$) and 250 ml of heptane are mixed at room temperature.

7.5 ml of 70% $HClO_4$ is rapidly added under vigorous stirring. The reaction mixture is stirred at room temperature for another 4 hours and the reaction is followed on HPLC. The epimeric distribution will eventually stop at 22R/22S=99/1. The reaction mixture is cooled and 10% aqueous $K_2CO_3$ is added. The temperature is not allowed to raise above 25° C. The reaction mixture is filtered and the solid residue is washed with 125 ml of heptane and 250 ml of $H_2O$ and stirred with methylene chloride to remove the product, which still was attached to the sand particles, and filtered.

The methylene chloride phase is washed with 50 ml of 10% aqueous $K_2CO_3$ and $2 \times 62,5$ ml of water, dried with $Na_2SO_4$ and concentrated in vacuum at 40° C., yielding 9,97 g of (22R)-16α,17α-butylidenedioxy-6α,-9α-difluoro-11β,21-dihydroxypregna-1,4-diene-3,20-dione mixed with 1,1% of the 22S-epimer. Molecular weight (MS-CI): 446. M.p. 169°–72° C. $[\alpha]_D^{25} = +94.5°$ (c=0.170; $CH_2Cl_2$). $^1$H-NMR ($CDCl_3$): 0.91 (18-$CH_3$), 4.59 (22-H), 4.93 (16-H).

EXAMPLE 4 (EMBODIMENT A)

Fluocinolone acetonide (2 g), 0,5 ml of propanol, 40 g of fine sand ($SiO_2$) and 50 ml of isooctane are mixed at room temperature.

1,5 ml of 70% $HClO_4$ is rapidly added under vigorous stirring. The reaction mixture is stirred at room temperature for another 5 hours and the reaction is followed on HPLC. The epimeric distribution will eventually stop at 22R/22S=96/4. The reaction mixture is cooled and 10% aqueous $K_2CO_3$ is added. The temperature is not allowed to raise above 25° C. The reaction mixture is filtered and the solid residue is washed with 20 ml of isooctane and 40 ml of $H_2O$ and stirred with methylene chloride to remove the product, which still was attached to the sand particles, and filtered.

The methylene chloride phase is washed with 10 ml of 10% aqueous $K_2CO_3$ and $2 \times 10$ ml of water, dried with $Na_2SO_4$ and concentrated in vacuum at 40° C., yielding 1,8 g of (22R)-6α,9α-difluoro-11β,21-dihydroxy-16α,17α-propylidenedioxypregna-1,4-diene-3,20-dione mixed with 4% of the 22S-epimer. Molecular weight (MS-CI): 452. M.p. 172°–83° C. $[\alpha]_D^{25} = +96.5°$ (c=0.2; $CH_2Cl_2$). $^1$H-NMR ($CDCl_3$): 0.93 (18-$CH_3$), 4.58 (22-H), 4.93 (16-H).

EXAMPLE 5 (EMBODIMENT A)

Triamcinolone acetonide (2 g), 0,6 ml of butanal, 40 g of fine sand ($SiO_2$) and 50 ml of isooctane are mixed at room temperature.

1,5 ml of 70% $HClO_4$ is rapidly added under vigorous stirring. The reaction mixture is stirred at room temperature for another 5 hours and the reaction is followed on HPLC. The epimeric distribution will eventually stop at 22R/22S=95/5. The reaction mixture is cooled and 10% aqueous $H_2CO_3$ is added. The temperature is anow allowed to raise above 25° C. The reaction mixture is filtered and the solid residue is washed with 20 ml of isooctane and 40 ml of $H_2O$ and stirred with methylene chloride to remove the product, which still was attached to the sand particles, and filtered.

The methylene chloride phase is washed with 10 ml of 10% aqueous $K_2CO_3$ and $2 \times 10$ ml of water, dried with Na₂SO₄ and concentrated in vacuum at 40° C., yielding 2 g of (22R)-16α,17α-butylidenedioxy-9α-fluoro-11,21-dihydroxypregna-1,4-diene-3,20-dione mixed with 5% of the 22S-epimer. Molecular weight (MS-CI): 448. M.p. 147°–50° C. $[\alpha]_D^{25} = +114.5°$ (c=0.2; CH₂Cl₂). ¹H-NMR (CDCl₃): 0.93 (18-CH₃), 4.59 (22-H), 4.91 (16-H).

EXAMPLE 6 (EMBODIMENT A)

16α-Hydroxyprednisolone 16,17-acetonide (0.50 g), butanal (0.32 ml) and 150 ml of methylene chloride are mixed. Perchloric acid (70%; 0.22 ml) is added at room temperature. The reaction mixture is stirred for 16 h at 33° C., cooled to room temperature, washed with 10% aqueous K₂CO₃ and water, dried and evaporated. The residue was precipitated from methylene chloride-petroleum ether yield 0.47 g of (22R)-11,21-dihydroxy-16α,17α-butylidenedioxypregna-1,4-diene-3,20-dione mixed with 5% of the 22S-epimer. Molecular weight (MS-CI): 430. M.p. 205-223° C. $[\alpha]_D^{25} = +111.8°$ (c=0.28; CH₂Cl₂).

EXAMPLE 7 (EMBODIMENT B)

16α-Hydroxyprednisolone 16,17-acetonide (1,0 g), chloroform (5 ml) and butanal (0,35 ml) are mixed at +0° C. Perchloric acid (70%; 0,5 ml) is added and the reaction is followed on HPLC. The epimeric distribution will eventually stop at 22R/22S 50/50. The reaction time is about 10 minutes. 3% K₂CO₃ and CH₂Cl₂ is added. The CH₂Cl₂-phase was washed with water, dried with Na₂SO₄ and evaporated (concentrated in vacuum) at +40°–+50° C. Yield: 1,0 g of (22R) 16α,17α-butylidenedioxy-11β,21-dihydroxypregna-1,4-diene-3,20-dione mixed with 45% of the 22S-epimer. Molecular weight (MC-CI): 430. M.p. 224°–231° C. $[\alpha]_D^{25} = +96.9°$ (c=0,2 in CH₂Cl₂).

EXAMPLE 8 (EMBODIMENT B)

16α-Hydroxyprednisolone 16,17-acetonide (1,0 g), chloroform (5 ml) and butanal (0,35 ml) are mixed at −10° C. Perchloric acid (70%; 0,5 ml) is added and the reaction is followed on HPLC. The epimeric distribution will eventually stop at 22R/22S 51/49. The reaction time is about 50 minutes. The reaction product is worked up as in Example 7. Yield: 1,0 g of (22R) 16α,17α-butylidenedioxy-11β,21-dihydroxypregna-1,4-diene-3,20-dione mixed with 51% of the 22S-epimer. Molecular weight (MC-CI): 430.

EXAMPLE 9 (EMBODIMENT B)

16α-Hydroxyprednisolone 16,17-acetonide (1,0 g), methylene chloride (5 ml) and butanal (0,35 ml) are mixed at −10° C. Perchloric acid (70%; 0,5 ml is added and the reaction is followed on HPLC. The epimeric distribution will eventually stop at 22R/22S 51/49. The reaction time is about 50 minutes. The reaction product is worked up as in Example 7. Yield: 1,0 g of (22R) 16α,17α-butylidenedioxy-11β,21-dihydroxypregna-1,4-diene-3,20-dione mixed with 51% of the 22S-epimer. Molecular weight (MC-CI): 430.

EXAMPLE 10 (EMBODIMENT B)

16α-Hydroxyprednisolone 16,17-acetonide (1,0 ), methylene chloride (6 ml), N,N-dimethylformamide (1 ml) and butanal (0,35 ml) are mixed at +20° C. Perchloric acid (70%; 0,5 ml) is added and the reaction is followed on HPLC. The epimeric distribution will eventually stop at 22R/22S 50/50. The reaction time is 20 h. The reaction product is worked up as in Example 7. Yield: 1,0 g of (22R) 16α,17α-butylidenedioxy-11β,21-dihydroxypregna-1,4-diene-3,20-dione mixed with 45% of the 22S-epimer. Molecular weight (MC-CI): 430.

We claim:

1. A method of controlling the epimeric distribution in the preparation of 16,17-acetals of pregnane derivatives having the formula I

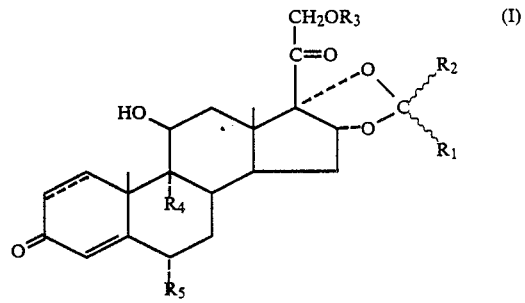

where in the 1,2-position is saturated or unsaturated;
R₁ represents a C₁–C₁₂ straight chain or branched alkyl;
R₂ is different from R₁ and may be hydrogen, methyl or ethyl;
R₃ may be hydrogen or

wherein R represents a C₁–C₁₂ straight chain or branched alkyl group;
R₄ may be hydrogen, fluorine or chlorine;
R₅ may be hydrogen, methyl, fluorine or chlorine, comprising the steps wherein the corresponding 16,17-acetonides or 16,17-diols are reacted with an aldehyde or ketone having the formula

R₁COR₂ or its acetals

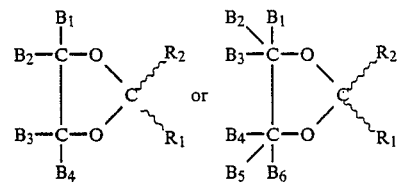

wherein R₁ and R₂ have the same meaning as in formula I and B₁–B₆ are the same or different and each representing hydrogen or an alkyl group with straight or branched hydrocarbon chains having 1–10 carbon atoms, in
(a) hydrocarbon solvent wherein the solubility of the pregnane derivative is less than 1 mg/l or in a halogenated hydrocarbon solvent together with a hydrohalogen acid or an organic sulphonic acid as catalyst and, when the solvent is a hydrocarbon, in the presence of small grains of an inert material or
(b) a halogenated hydrocarbon solvent together with a hydrohalogen acid or an organic sulphonic acid and as catalyst and in the presence of an epimeric distribution modifier selected from the group consisting of dimethylsulfoxide and N,N-dimethylformamide.

2. A method according to claim 1, characterized in that the 22R-epimer of 6-, 9- or 6,9-fluorinated and non-fluorinated (22RS)-16α,17α-butylidenedioxy-11β,21-dihydroxypregna-1,4-diene-3,20-diones and -4-pregnene-3,20-diones are previously by reaction of the corresponding 16,17-acetonides with n-butanal.

3. A method according to claim 1 characterized in that the molar ratio between steroidal acetal or diol and aldehyde or ketone ranges from 1:1 to 1:5.

4. A method according to claim 1 characterized in that the hydrohalogen acid catalyst is perchloric acid.

5. A method according to claim 1 characterized in that the hydrocarbon solvent is isooctane.

6. A method according to claim 1 characterized in that the halogenated hydrocarbon solvent is methylene chloride.

7. The method according to claim 1 wherein the epimeric distribution modifier is a temperature in the range of about 10° C. to 0° C.

* * * * *

UNITED STATES PATENT AND TRADEMARK OFFICE
CERTIFICATE OF CORRECTION

PATENT NO. : 4,925,933

DATED : May 15, 1990

INVENTOR(S) : Edib Jakupovic; Roy T. Sourander; Jan U. Stenbede; Rolf P. Svenson It is certified that error appears in the above-identified patent and that said Letters Patent is hereby corrected as shown below:

Cover page, right column, item [57] Abstract, Line 9, "insert" should read --inert--;
col. 3, line 46, "The $CH_2Cl$" should read --The $CH_2Cl_2$--;
col. 4, line 5, "stirring the" should read --stirring with--;
col. 4, line 25, "condition" should read --conditions--;
col. 4, line 32, "direction" should read --directing--;
col. 4, line 61, "reaction is" should read --reaction as--;
col. 5, line 21, "in" should read --on--;
col. 6, line 61, "$H_2CO_3$" should read --$K_2CO_3$--;
col. 6, line 61, "anow" should read --not--;
col. 7, line 17, "yield" should read --yielding--;
col. 7, lines 32-34, "16α, 1-7α-butylidenedioxy-11β, 21-dihydroxypregna-1, 4-diene-3, 20-dione" should read --16α, 17α-butylidenedioxy-11β, 21-dihydroxypregna-1, 4-diene-3, 20-dione--;
col. 7, lines 45-47, "16α1-7α-butylidenedioxy-11β, 21-dihydroxypregna-1, 4-diene-3, 20-dione" should read --16α, 17α-butylidenedioxy-11β, 21-dihydroxypregna-1, 4-diene-3, 20-dione--;
col. 8, line 67, claim 1(b), "and as catalyst" should read --as catalyst--;
col. 9, line 7, claim 2, "previously" should read --prepared--;

UNITED STATES PATENT AND TRADEMARK OFFICE
CERTIFICATE OF CORRECTION

PATENT NO. : 4,925,933

DATED : May 15, 1990

INVENTOR(S) : Edib Jakupovic; Roy T. Sourander; Jan U. Stenbede; Rolf P. Svenson It is certified that error appears in the above-indentified patent and that said Letters Patent is hereby corrected as shown below:

col. 2, lines 10-35    should read --

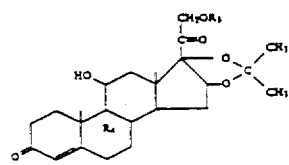

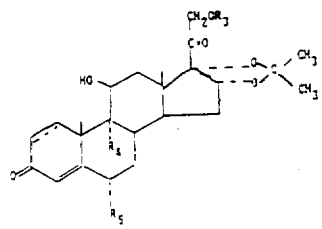

or

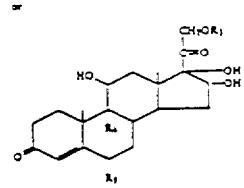

or

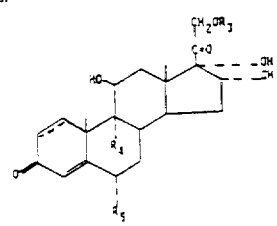

--;

Signed and Sealed this

Tenth Day of May, 1994

Attest:

BRUCE LEHMAN

Attesting Officer

Commissioner of Patents and Trademarks